US00PP20366P2

(12) United States Plant Patent
Utecht

(10) Patent No.: US PP20,366 P2
(45) Date of Patent: Sep. 29, 2009

(54) *PELARGONIUM* PLANT NAMED 'FISHELSH'

(50) Latin Name: *Pelargonium×hortorum*
Varietal Denomination: Fishelsh

(75) Inventor: Angelika Utecht, Montabaur (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/229,140

(22) Filed: Aug. 20, 2008

(51) Int. Cl.
*A01H 5/00* (2006.01)

(52) U.S. Cl. ..... Plt./327

(58) Field of Classification Search ..... Plt./325, Plt./327
See application file for complete search history.

(56) References Cited

U.S. PATENT DOCUMENTS

PP19,058 P2 * 7/2008 Utecht ..... Plt./327

OTHER PUBLICATIONS

UPOV-ROM GTITM, Plant Variety Database, 2009/01 GTI Jouve Retrieval Software, citation for 'Fishelsh'.*

* cited by examiner

*Primary Examiner*—Susan B McCormick Ewoldt
(74) *Attorney, Agent, or Firm*—S. Matthew Edwards

(57) ABSTRACT

A new *Pelargonium* plant named 'Fishelsh,' particularly distinguished by the round, semi-double, salmon-pink flowers, umbels on relatively long peduncles, medium green foliage with relatively strong leaf zone, medium to tall sized, rounded plant habit with the flower heads well above the foliage, and early to medium spring flowering response.

1 Drawing Sheet

Latin name of the genus and species of the plant claimed: *Pelargonium×hortorum.*

Varietal denomination: 'Fishelsh'.

BACKGROUND OF THE NEW PLANT

The present invention comprises a new zonal *Geranium,* botanically known as *Pelargonium×hortorum,* and hereinafter referred to by the variety name 'Fishelsh.'

'Fishelsh' is a product of a planned breeding program. The new cultivar has salmon-pink, semi-double flowers, medium green, distinctly zoned foliage, medium sized to tall plant habit with the flower heads relatively high above the foliage.

'Fishelsh' originated from a hybridization made in the late summer of 2002 in a controlled breeding program in Hillscheid, Germany. The female parent was an unpatented hybrid seedling 'K93-484-4' with light salmon, single-type flowers, and dark-green foliage with strong zonation.

The male parent of 'Fishelsh' was an unpatented hybrid seedling identified as 'K93-401-15' with light salmon, semi-double flowers, and dark green foliage.

'Fishelsh' was selected as one flowering plant within the progeny of the stated cross in the spring of 2003 in a controlled environment in Galdar, Gran Canaria, Spain.

The first act of asexual reproduction of 'Fishelsh' was accomplished when vegetative cuttings were taken from the initial selection in the fall of 2003 in a controlled environment in Galdar, Gran Canaria, Spain.

Horticultural examination of plants grown from cuttings of the plant initiated in March of 2004 in Hillscheid, Germany, and continuing thereafter, has demonstrated that the combination of characteristics as herein disclosed for 'Fishelsh' are firmly fixed and are retained through successive generations of asexual reproduction.

'Fishelsh' has not been observed under all possible environmental conditions. The phenotype may vary significantly with variations in environment such as temperature, light intensity and day length.

Plant Breeder's Rights for this cultivar was applied for in Canada on Mar. 30, 2007, in Germany on Feb. 21, 2007, and in the European Union on Jun. 20, 2008. 'Fishelsh' has not been made publicly available more than one year prior to the filing of this application.

DESCRIPTION OF THE DRAWING

The accompanying photographic drawing shows typical flower and foliage characteristics of 'Fishelsh' with colors being as true as possible with an illustration of this type. The photographic drawing shows a flowering potted plant, about 3–4 months old, of the new variety.

DETAILED BOTANICAL DESCRIPTION

The measurements were taken in Hillscheid, Germany, on May 9, 2007 on 9 week old plants that were growing in a greenhouse. Culture of these plants had started in early March when rooted cuttings were planted 12 cm pots and were grown out, without pinching, at an average day/night temperature of 14° C. until mid of April, and at higher temperatures thereafter.

Color Chart used: The Royal Horticultural Society Colour Chart (R.H.S.) 2001

BRIEF SUMMARY OF INVENTION

The following observations, measurements, and comparisons describe plants grown indoors in Hillscheid, Germany, and in Chatellerault, France. The following traits have been repeatedly observed and are determined to be basic characteristics of the new variety. The combination of these characteristics distinguishes this *Pelargonium* (common name zonal *Geranium*) as a new and distinct variety.

1. Salmon-pink and white flower color
2. Round, semi-double flowers
3. Medium to large inflorescences on relatively long peduncles
4. Medium green foliage with medium to strong zonation
5. Medium vigor, mounding, well-branched plant habit
6. Early to medium spring flowering response
7. Suitable as a bedding plant and for container planting

TABLE 1

DIFFERENCES BETWEEN THE NEW VARIETY 'FISHELSH' AND SIMILAR VARIETIES:

| | 'Fishelsh' | 'Schöne Helena' (U.S. Plant Pat. No. 5,374, no longer in force) | 'Fishelus' (U.S. Plant Pat. No. 16,934) |
|---|---|---|---|
| Overall flower color | Slightly less orange, more pink hue, RHS 43C to 52D, near margins color marbled/mixed with pale pink | Slightly more salmon-orange, RHS 44D, with distinct, nearly white margins | More salmon-orange hue, RHS 41B, somewhat lighter at margins |
| Length of peduncles, outdoors | 16-20 cm | 17-22 cm | 14-18 cm |
| Leaf zone, distinctness (from 1 absent to 9 very strong) | 5-7 | 2 | 5 |

Plant:

*Form, growth and habit.*—Medium vigor, mounding and well-branched.

*Plant height.*—15.7 cm.

*Plant height* (*inflorescence included*).—23.0 cm.

*Plant width.*—27.2 cm.

*Plant height at the end of the summer.*—27 cm (6 months old, on August 28).

*Plant width at the end of the summer.*—About 30–35 cm in diameter.

Stem:

*Number of branches.*—7.3.

*Color of stem.*—Light green, RHS 143C, no anthocyanin.

*Length of stem.*—11–16 cm.

*Diameter.*—0.8–1.1 cm.

*Length of internodes.*—About 2–4 cm.

*Texture.*—Dense pubescence.

Foliage:

*Immature, leaf color, upper surface.*—RHS 137C. Lower surface: RHS 138A.

*Mature, leaf color, upper surface.*—Medium green, RHS 137C. Lower surface: Intermediate between RHS 138B and RHS 143C.

*Length.*—5.8 cm.

*Width.*—9.8 cm.

*Shape.*—Reniform (kidney-shape) with wide open base and with weak lobes, palmate venation.

*Base shape.*—Cordate.

*Apex shape.*—Rounded.

*Margin.*—Bi-crenate, a little wavy.

*Texture.*—Velvety, both surfaces covered with very short hair, somewhat stronger hairs along the protruding veins of the lower surface.

*Color of zone.*—Dark brown, RHS 166A to RHS 200B, distinctness medium to strong.

*Color of veins, upper surface.*—Indistinct, RHS 137D.

*Color of veins, lower surface.*—Pale green, RHS 145A.

*Petiole color.*—RHS 137D (upper side) to 138A (lower side).

*Petiole length.*—6–7 cm.

*Diameter of petiole.*—3–4 mm.

*Texture.*—Dense hair, hirtellous.

Inflorescence:

*Begin of flowering* (50% *of plants with open flowers*).—May 2 (8 weeks old).

*Duration of flowering.*—Continuously flowering throughout the summer.

*Number of inflorescences per plant.*—2–3; 13–15 in late summer.

*Type and shape of inflorescence.*—An umbel, semi-sphere.

*Number of flowers and buds per inflorescence.*—Approximately 30 to 50.

*Umbel diameter.*—9.4 cm.

*Umbel depth.*—5.5 cm.

*Color of peduncle.*—Light green, RHS 143C; Outdoors infusion with anthocyanin may occur: RHS 174A.

*Length of peduncle.*—15.5 cm.

*Peduncle diameter.*—4–5 mm.

*Texture.*—Densely covered with short hair.

*Color of pedicel.*—Mainly 143C to 144A, partly brownish, RHS 179B.

*Length of pedicel.*—2.2 cm.

*Diameter of pedical.*—1.5 mm.

*Texture.*—Densely covered with glandular hair.

Corolla:

*Form.*—Semi-double, nearly round, shallow cup-shape with inner petals and petaloids.

*Diameter of flower.*—4.3 cm.

*Depth of flower.*—1.2 cm.

*Number of petals.*—7–10.

*Color upper petals, upper-surface.*—RHS 43C, near margin lighter and more pink: from RHS 52D to 56D.

*Color upper petals, lower surface.*—Mainly RHS 56D, with deeper colored areas or stripes, RHS 52C to 52D.

*Length of upper petals.*—2.4–2.6 cm.

*Width of upper petals.*—2.2–2.7 cm.

*Color lower petals, upper surface.*—RHS 43C, margin RHS 52D to 56D.

*Color lower petals, lower surface.*—Mainly RHS 56D, with deeper colored areas or stripes, RHS 52C to 52D.

*Length of lower petals.*—2.0–2.3 cm.

*Width of lower petals.*—1.9–2.3 cm.

*Petal shape.*—Obovate.

*Apex shape.*—Rounded.

*Margin.*—Entire or very weakly crenated in parts.

*Petal texture.*—Smooth, glabrous.

*Number of petaloids.*—2–4, narrow and shorter than petals, same color as petals.

*Color of petaloids.*—RHS 43C upper surface, RHS 49D lower surface.

Bud (just before opening):

*Color.*—RHS 37A to 38A, variable.

*Length.*—Approximately 15–19 mm.

*Width.*—8–9 mm.
*Shape.*—Elliptical, relatively narrow.

Calyx:
*Number of sepals.*—5.
*Color of sepals.*—Mainly RHS 144A to 144B for the visible surface, at base possibly weakly brownish: RHS 179B.
*Length of sepals.*—10–12 mm.
*Width of sepals.*—4 mm for the largest sepal, 2–3 mm for the other 4 sepals.
*Sepal shape.*—Lanceolate.
*Apex shape.*—Acute.
*Margins.*—Entire.
*Texture.*—Densely covered with glandular hair, and a few soft, longer hairs.

Reproductive organs:
*Pistil.*—One.
*Length.*—8 mm.
*Style color.*—RHS 47B to 47C.
*Style length.*—3–4 mm.
*Stigma color.*—RHS 43B.
*Number of anthers.*—Most often 5.
*Length of anthers.*—2–3 mm.
*Anther color.*—RHS 54A.
*Length filaments.*—7–8 mm.
*Color of filaments.*—White at base, RHS 52A at upper end.
*Pollen amount.*—Moderate.
*Color of pollen.*—Orange, RHS 28A.
*Fertility/seed set.*—No seed set observed.

Disease/pest resistance: Disease resistance or susceptibility other than typical for the species has not been observed on this hybrid.

What is claimed is:

1. A new and distinct variety of *Pelargonium* plant named 'Fishelsh,' substantially as illustrated and described herein.

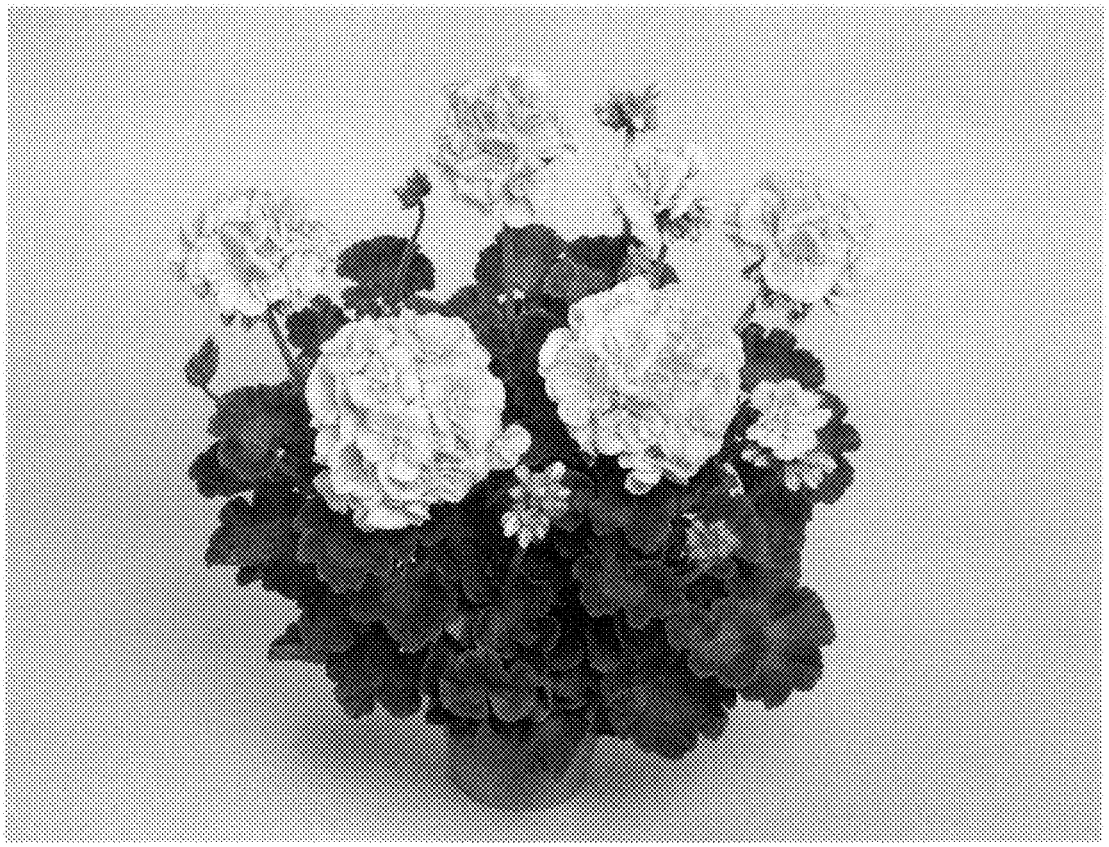

* * * * *